(12) United States Patent
Martin et al.

(10) Patent No.: US 6,979,458 B1
(45) Date of Patent: Dec. 27, 2005

(54) BEVERAGE AND ADDITIVE FOR WELLNESS

(75) Inventors: Kenneth A. Martin, 8907 Kanis Rd., Suite 330, Little Rock, AR (US) 72205; Teresa Leigh Barr, Port Townsend, WA (US)

(73) Assignee: Kenneth A. Martin, Maumelle, AR (US)

( * ) Notice: Subject to any disclaimer, the term of this patent is extended or adjusted under 35 U.S.C. 154(b) by 506 days.

(21) Appl. No.: 10/241,544

(22) Filed: Sep. 11, 2002

(51) Int. Cl.[7] .............................................. A61K 47/00
(52) U.S. Cl. ..................... 424/439; 424/725; 426/72; 426/74; 514/62
(58) Field of Search ................. 424/54, 476, 466, 424/439; 426/72, 74; 514/62

(56) References Cited

U.S. PATENT DOCUMENTS

| | | | |
|---|---|---|---|
| 4,647,453 A * | 3/1987 | Meisner ........................ | 424/54 |
| 5,827,834 A | 10/1998 | Falk ............................. | 514/54 |
| 5,852,002 A | 12/1998 | Falk ............................. | 514/54 |
| 5,929,048 A | 7/1999 | Falk ............................. | 514/54 |
| 5,932,560 A | 8/1999 | Falk ............................. | 514/54 |
| 6,194,392 B1 | 2/2001 | Falk ............................. | 514/54 |
| 6,391,864 B1 * | 5/2002 | Stone ........................... | 514/62 |
| 6,399,093 B1 | 6/2002 | Petrus .......................... | 424/448 |
| 6,589,555 B2 * | 7/2003 | Pandya ........................ | 424/466 |
| 6,660,308 B1 * | 12/2003 | Martin et al. ................ | 424/728 |

\* cited by examiner

Primary Examiner—Thurman K. Page
Assistant Examiner—Micah-Paul Young
(74) Attorney, Agent, or Firm—Buskop Law Group, P.C.; Wendy Buskop

(57) ABSTRACT

The invention is an ingestible wellness one time daily dosage made of a large quantity of rapid absorbing glucosamine sulfate, glucosamine hydrochloride, and an n-acetyl glucosamine and combinations thereof, a large quantity of chondroitin sulfate, chondroitin hydrochloride and combinations thereof, a vasodialating sulfonate with at least one methyl group, and a buffer to reduce adverse symptoms from large amounts of glucosamine and chondroitin selected from the family of araliaceae and a B3 vitamin, wherein the invention is also a wellness beverage that involves a fluid combined with the ingestible wellness dosage.

8 Claims, No Drawings

BEVERAGE AND ADDITIVE FOR WELLNESS

FIELD OF THE INVENTION

The present invention is an ingestible wellness dosage used to promote wellness in the ill, reinforce tissue strength, and maintain joint health. The present invention is also a wellness beverage in which the ill can receive their daily dosage through a single intake of a fluid that contains the wellness dosage.

BACKGROUND OF THE INVENTION

A need has existed for a large convenient dosage that is not in a solid form of glucosamine, chondroitin and MSM to be taken in one daily dose that can be quickly absorbed into the bloodstream, thereby bypassing the gut and eliminating the adverse reactions to the elemental ingredients as well as protecting and buffering the lining of the stomach from the high dosages of the ingredients as well as buffering the glucose levels, in the blood, therefore significantly reducing or eliminating the adverse effects of the essential ingredients, and making it possible to administer a one time daily large dose that is fast absorbing, using a powerful vasodilatation system, is tasteless in most liquids, odorless, non-steroidal, has no adverse symptoms of nausea, heartburn, diarrhea, constipation or headache as well as perfusing underperfused tissue by saturating the tissue, increasing mobility of a mammal in all directions, decreasing inflammation, maintain cartilage viability, increase strength, muscle flexibility and endurance that is also cost effective and capable of mass production.

Petrus U.S. Pat. No. 6,399,093 discloses a method and composition for the treatment of musculoskeletal disorders in mammals by the application of a topical composition comprising a permeation enhancing amount of one or more penetration enhancers, and one or more bio-affecting agents to provide anti-inflammatory relief and analgesia to the applied body part.

Falk U.S. Pat. No. 6,194,392 discloses a method of topically applied preparation that relieves pain and includes analgesics using hyaluronic acid in the range of 150,000 to 750,000 daltons where the form of hyaluronic acid is sufficient to provide a dosage greater than 10 mg and less than 3000 mg. Falk U.S. Pat. Nos. 5,827,834; 5,852,002; 5,929,048; and 5,932,560 refer to methods of using MSM, hyaluronic acid and glucosamine to reduce the swelling of brain tumors in a similar manner as Falk U.S. Pat. No. 6,194,392.

Glucosamine and chondrointin have been touted recently as a supplement for joint and cartilage health. The present invention relates to placing glucosamine and chondrointin in a suspension agent, like corn syrup, high fructose corn syrup, glycerin, glucose, sucrose, can be readily added to juices during manufacture for the mass market and, therefore easy to use and a desirable supplement form for the public.

Some of the chemicals used in this invention are described in the following paragraphs.

Glucosamine, whose scientific name is 2-amino-2-deoxyglucose sulfate, occurs naturally in the human body. Glucosamine provides strength, flexibility, and elasticity to cartilage and connective tissue by stimulating the production of glycosaminoglycans. Glucosamine also decreases inflammation that can lead to joint destruction. Glucosamine is involved in the formation of nails, tendons, skin, eyes, bones, ligaments, and heart valves. More importantly, it contributes to the strength and integrity of joint structures.

Connective tissue and cartilage naturally contain high concentrations of glucosamine. When sufficient levels of glucosamine are present, cartilage retains its ability to hold water and act as a shock absorber. Glucosamine sulfate is a simple molecule composed of glucose, an amine, and sulfur. The joints are naturally rich in sulfur molecules, which form important cross-linkages with other molecules. These cross-linkages provide cartilage with its strength, structure, and shock-absorbing qualities. That's one reason glucosamine sulfate is the preferred form of supplemental glucosamine. Another reason is absorbability.

Each person produces a certain amount of glucosamine in his or her bodies. As people age, their bodies no longer produce enough glucosamine causing arthritic conditions such as deformed joints and limited joint movement. Numerous double-blind, placebo controlled, glucosamine studies have been published, all reporting that glucosamine was indeed very effective in treating osteoarthritis and that its use is long-term safe. The studies have also shown that glucosamine provided in liquid form is absorbed more quickly, much more fully, and provides greater and longer lasting relief.

Chondroitin sulfate, whose scientific name is chondroitin 4-sulfate and chondroitin 4- and 6-sulfate, belongs to a class of very large molecules called gycosaminoglycans (GAGs). Chondroitin is manufactured from natural sources, such as shark, bovine and other cartilage extracts and is made up of repeating units of glucosamine with attached sugars. The molecules in these formulas are 250 times larger than glucosamine sulfate. Chondroitin is used for arthritic conditions because it is endogenously found in cartilaginous tissues in most mammals and serves as a substrate for the formation of joint matrix structure. Adverse reactions include epigastric pain, nausea, diarrhea and constipation.

Methylsulfonylmethane (MSM) is a natural form of organic sulfur found in all living organisms. MSM is prevalent throughout the human body. MSM is an important food that plays many roles in the body, including the stimulation of the growth of healthy skin, hair and nails. It is needed by the body for healthy, connective tissues and joint function, proper enzyme activity and hormone balance, along with the proper function of the immune system. MSM is highly soluble in both oil and water. As oxygen is transported from the lungs to the mitochondria, it goes through a number of stages with continually decreasing oxidation potential or effective oxygen concentration. MSM easily and rapidly diffuses through the hydrophilic cell cytoplasm as well as the hydrophobic cell membranes. MSM has no barriers. The human body has no other molecules naturally occurring in our bodies similar to MSM. Oxygen transport is handled by passing it between different molecules that are hydrophilic in the cytoplasm and hydrophobic in the cell membranes.

Hyaluronic acid, also called sodium hyaluronate, or hyaluronan or HA, is a linear polysaccharide composed of repeating disaccharide units of N-acetyl-glucosamine and D-glucuronic acid. The highest concentrations of HA are found in the soft connective tissue where it is a major component of the extra cellular matrix. HA is present in hyaline cartilage, in synovial joint fluid, and in the skin tissue, both dermis and epidermis. Injecting substances with HA into the knee joint provides long-term pain relief for some people with osteoarthritis. Hyaluronic acid is a natural component of cartilage and joint fluid. HA lubricates and absorbs shock in the joint. The Food and Drug Administration (FDA) recently approved this therapy for patients with osteoarthritis of the knee if they do not get relief from exercise, physical therapy, or simple analgesics. Numerous clinical investigations have demonstrated the efficacy and safety of injecting of HA in the treatment of osteoarthritis of the knee and other large joints. These clinical studies demonstrated that treatment with HA results in significant improvement in a number of inflammatory and path physiological parameters.

Ginseng, in which the applicable part is the root, contains ginsenosides. Ginsenosides reportedly lower blood pressure; act as an anti-hemolytic, anti-pyretic, anti-psychotic, CNS depressant and ulcer protective activity; and increase GI mobility and decreases islet insulin concentrations. When used orally, ginseng reduces post-pranial blood glucose levels in type 2 diabetics. Ginseng has also been found to lower blood glucose levels and to enhance the efficacy of vitamins C, B and E. Ginseng also acts as an adaptogen, a substance that can act to strengthen the body and increase general resistance. Vitamin B3, or niacin comes in two forms, nicotinic acid and nicotinamide. The body manufactures niacin by utilizing the amino acid, tryptophan. Nicotinic acid is needed for the proper function of the nervous system and circulatory system. Nicotinamide metabolizes carbohydrates, fats, and proteins. Niacin contributes to more than fifty vital bodily processes. Including the conversion of food into energy, building red blood cells, and synthesizing hormones, fatty acids, and steroids. The body uses vitamin B3 in the process of releasing energy from carbohydrates.

Vitamin C is a water-soluble vitamin that is important in forming collagen, a protein that gives structure to bones, cartilage, muscle, and blood vessels. Vitamin C also helps maintain capillaries, bones, and teeth. It also aids in the absorption of iron. Vitamin C's crucial importance is in the maintenance of a healthy immune system. Large doses of vitamin C also help relax blood vessels and maintain blood flow.

Vitamin E, also known as tochopherol, is fat soluble and stored in the body in for a short term. The body uses Vitamin E as an anticoagulant and a temperature regulator. Vitamin E appears to play a significant role in boosting the immune system and acts as a powerful antioxidant that protects cell membranes. Vitamin E is essential to the body in order to help improve circulation, promote normal clotting, and allow the muscles to use oxygen.

The present invention is beneficial because it fast absorbing, tasteless, odorless, non-steroidal, and a vasodilator. The invention additive also is a one-time daily large dose. There are no symptoms of nausea, heartburn, constipation, diarrhea, and headaches associates with the present invention. In addition, the present invention contains a high quantity of glucosamine and a high quantity of choindroitin.

The beverage of the present invention is also cost effective since it is capable of being mass-produced. An eight ounce or twelve ounce beverage can contain the single serving daily dose.

The present invention is also beneficial because it perfuses underperufsed tissues. This means the additive saturates the tissue, increases mobility in all directions, decreases inflammation, maintains cartilage viability, increases strength, increases muscle flexibility, and increases endurance.

SUMMARY OF THE INVENTION

The invention is an ingestible wellness dosage made of a large quantity of glucosamine sulfate, glucosamine hydrochloride, and an n-acetyl glucosamine and combinations thereof The wellness dosage also includes a large quantity of chondroitin sulfate, chondroitin hydrochloride and combinations thereof, as well as, a member of the family of araliaceae, and a B3 vitamin.

The invention is another ingestible wellness dosage made of a large quantity of glucosamine sulfate, glucosamine hydrochloride, and an n-acetyl glucosamine and combinations thereof, This wellness dosage also includes a large quantity of chondroitin sulfate, chondroitin hydrochloride and combinations thereof, as well as, a vasodialiting sulfonate with at least one methyl group, and a member of the family of araliaceae.

The invention is also a wellness dosage made of a fluid and a dosage amount in an ingestible amount for reinforcing tissue strength and maintaining joint health. The dosage is made of a glucosamine sulfate, glucosamine hydrochloride, and an n-acetyl glucosamine and combinations thereof; chondroitin sulfate, chondroitin hydrochloride and combinations thereof; a member of the family of araliaceae; and a B3 vitamin.

The invention is also another wellness dosage made of a fluid and a dosage amount in an ingestible amount for reinforcing tissue strength and maintaining joint health. The dosage is made of glucosamine sulfate, glucosamine hydrochloride, and an n-acetyl glucosamine and combinations thereof; a chondroitin sulfate, chondroitin hydrochloride and combinations thereof; a sulfonate with at least one methyl group; and a member of the family of araliaceae.

DETAILED DESCRIPTION

Before explaining the present invention in detail, it is to be understood that the invention is not limited to the particular embodiments and that it can be practiced or carried out in various ways.

The invention is an ingestible wellness dosage made of a large quantity of glucosamine sulfate, glucosamine hydrochloride, and an n-acetyl glucosamine and combinations thereof The dosage also includes a large quantity of chondroitin sulfate, chondroitin hydrochloride and combinations thereof The final ingredients are a member of the family of araliaceae and a B3 vitamin.

The wellness dosage can also include the lubricating agent sodium hyaluronate. In another alternative, the dosage can include 1000–2000 mg of glucosamine, 500–1500 mg of chondroitin, 10–20 mg of B3, and 400–800 mg of a member of the family of araliaceae. The dosage can further include 500–3000 mg of Vitamin C. The dosage can further include 400–2000 mg of Vitamin E.

The araliaceae in the dosage can be panax ginseng, Siberian ginseng or American ginseng. The B3 vitamin in the dosage can be vasodialating niacin, vasodialating nicotinic acid or vasodialating niacinamide. The solubility agent in the dosage can be water, xanthan gum and water; fructose, corn syrup, glucose, sucrose or xanthan derivatives.

The invention is another ingestible wellness dosage made of a large quantity of glucosamine sulfate, glucosamine hydrochloride, and an n-acetyl glucosamine and combinations thereof This dosage further includes a large quantity of chondroitin sulfate, chondroitin hydrochloride and combinations thereof, a vasodialating sulfonate with at least one methyl group, and a member of the family of araliaceae.

This dosage can further include the lubricating agent sodium hyaluronate.

This dosage can further include 1000–2000 mg of glucosamine, 500–1500 mg of chondroitin, 250–3000 mg of a sulfonate with at least one methyl group, and 400–800 mg of a member of the family of araliaceae. The dosage can also include 500–3000 mg of Vitamin C. In addition, the dosage also 400–2000 mg of Vitamin E.

The araliaceae in this dosage can be panax ginseng, Siberian ginseng or American ginseng. The B3 vitamin in this dosage can be vasodialating niacin, vasodialating nicotinic acid or vasodialating niacinamide. The solubility agent in this dosage can be water, xanthan gum and water; fructose, corn syrup, glucose, sucrose or xanthan derivatives. The sulfonate in this dosage can be at least one methyl group is methyl sulfonyl methane (MSM).

The invention also contemplates a wellness beverage. The wellness beverage is made of a fluid and a dosage amount in an ingestible amount for reinforcing tissue strength and maintaining joint health. The dosage amount includes a glucosamine sulfate, glucosamine hydrochloride, and an n-acetyl glucosamine and combinations thereof, chondroitin sulfate, chondroitin hydrochloride and combinations thereof, a member of the family of araliaceae, and a B3 vitamin.

The B3 vitamin in the wellness beverage can be is niacin. The araliaceae in the wellness beverage can be American ginseng, Siberian ginseng, or Panax ginseng. The fluid in the wellness beverage can be water, coffee, tea, artificial drinks, alcoholic fluids, non-alcoholic fluids, fruit juice, vegetable juice, blends of juice, juice and water blends, concentrates of juice, soda, sports drinks or combinations thereof.

The beverage can further include a lubricating agent sodium hyaluronate. The beverage can also further involve 1000–2000 mg of glucosamine, 500–1500 mg of chondroitin, 10–20 mg of B3, and 400–800 mg of a member of the family of araliaceae.

The invention further contemplates a wellness beverage that is a fluid and a dosage amount in an ingestible amount for reinforcing tissue strength and maintaining joint health. The dosage is made of glucosamine sulfate, glucosamine hydrochloride, and an n-acetyl glucosamine and combinations thereof, a chondroitin sulfate, chondroitin hydrochloride and combinations thereof, a sulfonate with at least one methyl group, and a member of the family of araliaceae.

The sulfonate with at least one methyl group of the above beverage can be methyl sulfonyl methane (MSM). The araliaceae of the above beverage can be American ginseng, Siberian ginseng, or Panax ginseng. The fluid used in the beverage can be water, coffee, tea, artificial drinks, alcoholic fluids, non-alcoholic fluids, fruit juice, vegetable juice, blends of juice, juice and water blends, concentrates of juice, soda, sports drinks or combinations thereof.

The beverage can further include the lubricating agent sodium hyaluronate. In addition, the beverage can contain 1000–2000 mg of glucosamine, 500–1500 mg of chondroitin, 250–3000 mg of sulfonate with at least one methyl group, and 400–800 mg of a member of the family of araliaceae.

While this invention has been described with emphasis on the preferred embodiments, it should be understood that within the scope of the appended claims, the invention might be practiced other than as specifically described herein.

What is claimed is:

1. An ingestible wellness dosage of a fluid consisting of:
   a. from 1000 mg to 2000 mg of a glucosamine sulfate, a glucosamine hydrochloride, and an n-acetyl glucosamine and combinations thereof;
   b. from 500 mg to 1500 mg of a chondroitin sulfate, a chondroitin hydrochloride and combinations thereof;
   c. from 400 mg to 800 mg of a member of the family of araliaceae; and
   d. from 10 mg to 20 mg of a B3 vitamin.

2. The dosage of claim 1, wherein said member of the family of araliaceae is a ginseng selected from the group: American ginseng, Siberian ginseng, and Panax ginseng.

3. The dosage of claim 1, wherein said B3 vitamin is selected from the group: vasodialating niacin, vasodialating nicotinic acid and vasodialating niacinamide.

4. A wellness beverage comprising:
   a. a fluid consisting of:
   b. a dosage amount in an ingestible amount for reinforcing tissue strength and maintaining joint health, wherein said dosage comprises:
      i. from 1000 mg to 2000 mg of a glucosamine sulfate, a glucosamine hydrochloride, and an n-acetyl glucosamine and combinations thereof;
      ii. from 500 mg to 1500 mg of a chondroitin sulfate, a chondroitin hydrochloride and combinations thereof;
      iii. from 400 mg to 800 mg of a member of the family of araliaceae; and
      iv. from 10 mg to 20 mg of a B3 vitamin.

5. The beverage of claim 4, wherein said B3 vitamin is niacin.

6. The beverage of claim 4, wherein said member of the family of araliaceae is a ginseng selected from the group: American ginseng, Siberian ginseng, and Panax ginseng.

7. The beverage of claim 4, wherein said fluid is a member of the group: water, coffee, tea, alcoholic fluids, non-alcoholic fluids, fruit juice, vegetable juice, concentrates of juice, and combinations thereof.

8. An ingestible wellness dosage of a fluid consisting of:
   a. from 1000 mg to 600 mg of a glucosamine sulfate, a glucosamine hydrochloride, and an n-acetyl glucosamine and combinations thereof;
   b. from 500 mg to 1500 mg of a chondroitin sulfate, a chonldroitin hydrochloride and combinations thereof;
   c. from 400 mg to 800 mg of a member of the family of araliaceae;
   d. from 10 mg to 20 mg of a B3 vitamin;
   e. a lubricating agent sodium hyaluronate;
   f. 500 mg to 3000 mg of Vitamin C;
   g. 400 mg to 2000 mg of Vitamin E; and
   h. a solubility agent selected from the group consisting of water, xanthan gum and water, fructose, corn syrup, glucose, sucrose and xanthan derivatives.

* * * * *